United States Patent [19]

Baylis

[11] 3,970,655

[45] July 20, 1976

[54] PREPARATION OF PYRIDINE

[75] Inventor: Anthony B. Baylis, North Plainfield, N.J.

[73] Assignee: Celanese Corporation, New York, N.Y.

[22] Filed: July 29, 1974

[21] Appl. No.: 492,559

Related U.S. Application Data

[63] Continuation of Ser. No. 80,175, Oct. 12, 1970, abandoned.

[52] U.S. Cl. .............................................. 260/290 P
[51] Int. Cl.$^2$ ..................................... C07D 213/10
[58] Field of Search ................................... 260/290

[56] References Cited
UNITED STATES PATENTS 3,829,428   8/1974   Hargis................................ 260/290

FOREIGN PATENTS OR APPLICATIONS 900,799   7/1962   United Kingdom................. 260/290

OTHER PUBLICATIONS

Ishiguro et al., Chem. Abst., vol. 46, col. 504 e–f (1952).
Leitis et al., Chem. Abst., vol. 61, col, 4304f (1965).

Primary Examiner—Harry I. Moatz
Attorney, Agent, or Firm—John A. Shedden; Thomas J. Morgan

[57] ABSTRACT

Pyridine is prepared by reacting acetaldehyde, ammonia and oxygen at elevated temperatures and in the presence of a condensation catalyst, the oxygen (or air) oxidatively demethylating, in situ, the picolines and/or higher condensation products produced along with pyridine. A second embodiment includes incorporating methanol in the above reaction mixture. A third embodiment includes incorporating isobutyraldehyde in the above reaction mixture. These processes obviate the need for formaldehyde as a reactant.

4 Claims, No Drawings

PREPARATION OF PYRIDINE

This is a continuation of application Ser. No. 80,175 filed Oct. 12, 1970, now abandoned.

BACKGROUND OF THE INVENTION

Conventionally, pyridine and picolines are prepared from a reaction mixture comprising acetaldehyde, formaldehyde and ammonia using suitable catalysts, the aldehydes being the source of carbon. Since pyridine is in greater demand commercially than the picolines, it makes sound economic sense to try to enhance the pyridine-picoline product concentration in favor of pyridine. Furthermore, in view of the cost of formaldehyde, it would be quite advantageous to obviate its need or to substitute it with a less expensive reactant. Of course, still greater economy could be realized if any unused portions of the reactant substitute for formaldehyde could be recovered and recycled to subsequent reactant mixtures. This is not practical with present syntheses using formaldehyde, a handicap which represents considerable loss to the industry.

Pursuant to the present invention the disadvantages hereinbefore mentioned and other similar drawbacks which will become apparent are surmounted. These and a number of other advantages over the present art will be seen more clearly from the description which follows.

SUMMARY OF THE INVENTION

According to the present invention pyridine is prepared by reacting acetaldehyde, ammonia and oxygen at elevated temperatures and in the presence of a condensation catalyst. Condensation of these reactants is conducted in a vapor phase and preferably in the presence of an inert diluent, such as steam or nitrogen gas, or both. The term "oxygen" used herein is intended to include air as well, the latter containing a goodly portion of nitrogen which, of course, acts as an inert diluent.

Under normal circumstances, i.e., without adding oxygen or air, the product mixture would contain very little pyridine, if any. Essentially only 2-, 3-, 4-picolines would be produced along with higher condensation products, such as the methyl ethyl pyridines (MEP). The presence of oxygen in the reaction mixture causes in situ oxidative demethylation of the picolines and MEP to pyridine.

Pursuant to a second embodiment II of the present invention, acetaldehyde, methanol and ammonia are co-condensed in the presence of oxygen or air under the conditions given just above wherein no methanol is present. As is evident, the formaldehyde reactant presently employed in the synthesis of pyridine is replaced by the far less expensive methanol. Of course, the oxygen present in the reaction mixute oxidizes and demethylates, in situ, the picolines and higher condensation products formed along with pyridine. In addition, and contrary to the situation when formaldhyde is used, any unused methanol is readily recoverable and can be recycled. This, of course, represents a substantial saving.

According to a still further embodiment III of the instant discovery, acetaldehyde, ammonia, oxygen and isobutyraldehyde are reacted under the conditions given above to produce pyridine, the isobutyral being substituted for the more expensive formaldehyde and the oxygen reactant oxidatively demethylating, in situ, the picolines and higher condensation products formed along with pyridine. Thus, of course, the yield of pyridine is substantially enhanced.

Embodiment II and III just described are likewise best carried out in the presence of an inert diluent, such as $N_2$, steam, and the like. While these are the preferred diluents, other inert diluents include helium, argon, and the like, as well as saturated hydrocarbons, such as methane, ethane, propane, etc.

DETAILED DESCRIPTION OF THE INVENTION

Reaction of any of the above embodiments is best carried out in the presence of a condensation catalyst of the silica-alumina type. In general, catalysts suitable for the reactions of the present invention are the aldehyde-ammonia condensation catalysts of the art. Typical aldehyde-ammonia condensation catalysts described in the prior art include aluminas, silicas, silica-aluminas, metal oxides, e.g., $z_rO_2$, $MgO$, $TiO_2$, $ThO_2$, $CuO$, $ZnO$, $PbO$, and the like. Preferred, however, are the silica-alumina catalyst containing either 13% or 25% $Al_2O_3$ and 87% or 75% $SiO_2$, by weight, respectively, and "doped" with other materials, particularly oxides and fluorides. Such doping materials include zinc oxide, $ZrO_2$, $ThO_2$, $BaO$, $CuO$, lead oxide, cadinium oxide, $MgO$ and fluorides, such as $ZnF_2$, $PbF_2$, $CdF_2$, $HF$, $NH_4F$, and the like. Other aldehyde-ammonia condensation catalysts within the purview of the present invention are the crystalline aluminio-silicates, for example, zeolites of the faujasite and mordenite families, naturally-occurring or synthetic, the latter also known as "molecular sieves".

While temperatures in the range of about 300° to about 550°C are suitable for all the reactions of the present invention, best results are achieved in a temperature range of about 350° to about 500°C. While very good results are achieved at atmospheric pressure, subatmospheric or superatmospheric pressures may be employed with corresponding reductions or increases in temperature, respectively.

The ratios of reactants best suited for embodiment I of the present invention, viz. the acetaldehyde, ammonia and oxygen reaction in the presence of an inert diluent, will now be discussed. The ranges are, on the basis of moles of each reactant and inert diluent per mole of acetaldehyde reactant, as follows:

Ammonia, about 0.2 to about 15.0 moles/mole acetaldehyde
Oxygen, about 0.1 to about 5.0 moles/mole acetaldehyde
Inert diluent, about 1.0 to about 25.0 moles/mole acetaldehyde.

When air is used in place of pure oxygen, the amount of air employed is controlled such that the oxygen to acetaldehyde molar ratio remains in the above range of about 0.1 to about 5.0 moles. The preferred molar amounts of reactants per mole of acetaldehyde are as follows:

Ammonia, about 0.5 to about 5.0 moles;
Oxygen, about 0.2 to about 2.5 moles;
Inert diluent, about 1 to about 10.0 moles.

It is generally preferred that the molar concentration of acetaldehyde in the total gaseous feed passing over the catalyst does not exceed about 30 to about 40%.

The residence time of the reactants over the catalyst may vary widely depending on the temperature, flow rate and whether the catalyst is in the fixed bed or fluidized form. Generally, residence times in the range of about 1 to about 60 seconds are employed and with a fixed bed catalyst the preferred range is between about 1 and about 15 seconds.

In embodiment II of the instant discovery, viz., the acetaldehyde, methanol, ammonia, oxygen (air) and inert diluent system, the moles of each reactant used per mole of acetaldehyde are in the ranges as follows:

Ammonia, from about 0.2 to about 15 moles;
Methanol, from about 0.1 to about 20 moles;
Oxygen, from about 0.1 to about 5.0 moles; and
Inert diluent, from about 1 to about 25 moles.

When air is used in place of pure oxygen, the amount of air employed is controlled such that the oxygen to acetaldehyde molar ratio remains in the above range of about 0.1 to about 5.0 moles. When operating the invention at high methanol levels, it is often convenient to run in the absence of added diluent, such as steam or nitrogen. The preferred molar amounts of reactants per mole of acetaldehyde are as follows:

Ammonia, from about 0.5 to about 5.0 moles;
Oxygen, about 0.2 to about 2.5 moles;
Methanol, about 0.25 to about 5.0 moles; and
Inert diluent, about 1 to about 10.0 moles.

When operating in the absence of inert diluent, the preferred methanol concentration is in the range about 1 to about 15 moles per mole of acetaldehyde.

In embodiment III, viz., the reaction of acetaldehyde, isobutyraldehyde, ammonia and oxygen (air) in the presence of an inert diluent, the moles of each reactant used per mole of acetaldehyde are in the ranges as follows:

Ammonia, about 0.2 to about 15 moles;
Oxygen, about 0.1 to about 5.0 moles;
Isobutyraldehyde, about 0.25 to about 10.0 moles; and
Inert diluent, about 1 to about 25 moles.

When air is used in place of pure oxygen the amount of air employed is controlled such that the oxygen to acetaldehyde molar ratio remains in the above range of about 0.1 to about 5.0. The preferred molar amounts of reactants per mole of acetaldehyde are as follows:

Ammonia, about 0.5 to about 5.0 moles;
Oxygen, about 0.2 to about 2.5 moles;
Isobutyraldehyde, about 0.5 to about 2.5 moles; and
Inert diluent, about 1 to about 10.0 moles.

As in embodiment I, above, it is generally preferred in embodiments II and III that the molar concentration of acetaldehyde in the total gaseous feed passing over the catalyst does not exceed about 30 to about 40%.

The residence time of the reactants over the catalyst may vary widely depending on the temperature, flow rate and whether or not the catalyst is employed in the fixed bed or the fluidized form. Generally residence times in the range of about 1 to about 60 seconds are employed and with a fixed bed catalyst the preferred range is in between 1 and 15 seconds.

For the most part, the sequence of addition of the reactants is not critical. However, in order to prevent blocking of the reactor it is advisable to preheat the aldehydes and ammonia to at least about 200°C before mixing. In general, the diluent ($N_2$, steam, etc.) is mixed with the aldehyde prior to mixing with the ammonia. When steam is used as a diluent it is convenient to use an aqueous acetaldehyde solution as feed (embodiment I) or an aqueous solution of acetaldehyde and methanol as feed (embodiment II). In embodiment III, where the butyraldehyde and water are not miscible it is convenient to use a mixed acetaldehyde/isobutyraldehyde feed and to add the water in the form of steam to the vaporized acetaldehyde/isobutyraldehyde stream. After mixing the diluent, aldehydes (and the methanol) with ammonia at about 200°C or above, the combined gaseous mixture is then preheated, to reaction temperature and mixed with the preheated oxygen (air) at a point just beneath the catalyst bed. After passing over the catalyst the emergent gases are condensed to the liquid form and analyzed by conventional techniques.

Prior to mixing the components, the catalyst is usually heated at reaction temperature for about 1 hour with a very slow flow of oxygen (air) passing over it. Immediately prior to admitting the aldehyde vapor the ammonia is allowed to flow over the catalyst along with the low oxygen (air) flow.

In order to better understand the examples and tables which follow, it is best to know the types of catalysts used and the method of preparing same, which catalysts are referred to by the letters A through M.

CATALYST PREPARATION

Catalyst A. 297 grams of 70% $HNO_3$ were added to a warm solution of 472.5 grams of $Na_2SiO_3.9H_2O$ dissolved in 2 liters of water (Part I). To 134.0 grams $Al(NO_3)_3 9H_2O$ dissolved in excess water was added a solution of 3.65 grams zinc oxide dissolved in approximately 15 cc. of 70% $HNO_3$ (Part II). To prepare the catalyst, the solution constituting Part II above was added rapidly with good agitation to the warmed solution constituting Part I above. After thorough mixing of the two parts, the entire solution was treated with $NH_4OH$ solution until the pH of the solution reached 9.5. After thorough mixing the resulting recipe was allowed to settle and the precipate was then filtered off. After filtering, the solid was washed thoroughly 2 or 3 times with water and dried at 200°C for three hours. The dried material was then calcined for 4 hours at 500°C.

Catalyst B. To 33 grams of catalyst A was added a solution containing 4.8 grams of 49% HF solution in 125 cc. $H_2O$. After steeping for 4 hours the solution was drained off, the catalyst washed with water and dried for 16 hours at 125°C.

Catalyst C. is prepared by heating catalyst B above for 16 hours in a furnace controlled at 475°C.

Catalyst D. was prepared by adding 168.53 grams of 10/20 mesh size, grade 980*, silica-alumina containing 13% alumina to a solution of 14.54 grams of 49% HF solution in 160 cc. $H_2O$. The mixture was allowed to steep at room temperature for 3 hours. After draining off any excess liquid the catalyst was heated overnight at 165°C.

*Sold by Davison Chemical Division of W. R. Grace & Co.

Catalyst E. To 942 grams of ⅛ inch pellets of grade 980* silica-alumina (13% alumina) was added a solution of 106.5 grams of 49% HF solution dissolved in 550 cc. $H_2O$. After steeping at room temperature for 6 hours the excess liquid was poured off and the catalyst was dried at 110°C for 16 hours. The dried catalyst was then calcined at 525°C for 6 hours before use.

Catalyst F. To 223 grams of ⅛ inch pellets of grade 980* silica-alumina (13% alumina) was added a solution of 35 grams Pb-(OOCCH$_3$)$_2$.3H$_2$O dissolved in 175 cc. H$_2$O. The catalyst was stirred for ½ hour, the excess liquid drained off and the catalyst dried at 120°C for 1 hour. To the dried catalyst containing the lead acetate was added a solution of 21.0 grams NH$_4$F dissolved in 175 cc. H$_2$O. After 5 minutes of agitation under reduced pressure the excess solution was poured off and the pellets washed free of soluble salts with water. After drying overnight at 120°C, the pellets were calcined for 3 hours at 450°C.

Catalyst G. This was prepared from catalyst A as follows: 22.2 grams of catalyst A was added rapidly to a solution containing 1.90 grams of 49% HF in 65 cc. water. After standing at room temperature for 2.5 hours the excess liquid was poured off and the catalyst was oven dried at 125°C. The catalyst was then heated for 4 hours in a furnace at 475°C.

Catalyst H. 69.3 grams of 10/20 mesh size Davison grade 980 silica-alumina containing 13% alumina were added rapidly to a solution containing 5.95 grams of 49% HF solution in 70 cc. water. After standing at room temperature for 5 hours, the excess liquid was poured off and the catalyst dried in an oven at approximately 125°C. Before using the catalyst, it was pretreated in the reactor at the reaction temperature for 0.5 to 1.0 hour under a low flow of air.

Catalyst J. 53.58 grams of 10/20 mesh size Davison grade 980 silica-alumina containing 25% alumina were added rapidly to a solution containing 4.63 grams of 49% HF solution in 60 cc. water. Drying and catalyst pre-treatment were the same as that described under catalyst H.

Catalyst K. This was prepared in two parts as follows:
Part 1. To 103.2 grams of 10/20 mesh size Davison grade 980 silica-alumina containing 25% alumina was added a solution containing 6.53 grams of 49% HF solution in 110 cc. water. After standing at room temperature for 4 hours, the excess liquid was decanted and the catalyst was dried for 3.5 hours at 165°C. After drying, the catalyst was calcined for 16 hours at 460°C.
Part 2. To 81.2 grams of the catalyst prepared in Part 1 was added a clear filtered solution of 29.85 grams of ZrO(NO$_3$)$_2$.2H$_2$O in 135 cc. water. The system was allowed to stand for 1 hour at room temperature and the water was then removed using a rotating evaporator while gently heating the flask under vacuum. After a final drying for 48 hours at 130°C the impregnated catalyst was calcined for 6 hours at 450°C.

Catalyst L. 34.3 grams of 10/20 mesh Davison Grade 980 silica-alumina containing 13% alumina was added to a solution containing 3.1 grams of 49% HF and 3.43 grams of Cu(NO$_3$)$_2$.3H$_2$O dissolved in 30 cc. water. The catalyst was allowed to steep in the Cu/HF solution for 5 hours with occasional agitation. After decanting the excess liquid, the catalyst was dried for 16 hours at 165°C and then calcined for 5 hours at 455°C.

Catalyst M. 50.0 grams of 10/20 mesh Davison grade 980 silica-alumina containing 13% alumina was added to 100 cc of a solution containing 5.0 grams thallium (1) acetate in 75 cc. ethanol/25 cc. water. NH$_4$OH solution was then added until the solution turned brown. The solvent was then removed by heating to 85°–90°C under vacuum. After drying for 16 hours at 150°C the catalyst was calcined for 2.0 hours at 500°C.

The present invention will best be understood from the following examples which, while specific and detailed, are intended to be illustrative only and not unduly limiting of the scope of the discovery.

EXAMPLES 1–15

The reactor used for these experiments was a 1-inch I.D. stainless steel tube, 6 inches long with threads at both ends. The material being used as catalyst was sandwiched midway up the reactor tube between two layers of glass beads. The reactor was sealed by means of threaded caps which screwed on both ends. Two entry holes were made opposite each other on one end of the reactor and a third hole for product effluent was made at the other end. The reactant vapors were mixed externally and passed directly into the bottom of the reactor via one of the two entry ports. The second entry port at the bottom of the reactor was used for the addition of the hot oxygen (air). The reactor was maintained at the desired temperature by immersion in a suitable heating medium. The following Table I illustrates embodiment I of the invention using the just-described reactor.

TABLE I

SYNTHESIS OF PYRIDINE AND PICOLINES FROM ACETALDEHYDE AND AMMONIA

| | | | | Gaseous Flow Rates (STP)$^r$ Mole/Hr/15 cc Catalyst | | |
|---|---|---|---|---|---|---|
| Example | Temp. °C | Catalyst | AcH** | H$_2$O | NH$_3$ | Air |
| 1 | 425 | A | 0.03769 | 0.2827 | 0.093 | 0.0493 |
| 2 | 425 | A | 0.03769 | 0.2827 | 0.0943 | 0.0830 |
| 3 | 425 | A | 0.02756 | 0.2067 | 0.0627 | 0.068 |
| 4 | 425 | B | 0.02756 | 0.2067 | 0.0627 | 0.068 |
| 5 | 425 | B | 0.01798 | 0.1798 | 0.1017 | 0.068 |
| 6 | 425 | B | 0.0220 | 0.220 | 0.066 | 0.066 |
| 7 | 425 | B | 0.01786 | 0.1786 | 0.0761 | 0.0456 |
| 8 | 425 | B | 0.01505 | 0.1505 | 0.07522 | 0.07522 |
| 9 | 425 | C | 0.01505 | 0.1505 | 0.0451 | 0.1053 |
| 10 | 425 | C | 0.01505 | 0.1505 | 0.07522 | 0.07522 |
| 11 | 388 | D | 0.015 | 0.150 | 0.075 | 0.075 |
| 12 | 420 | D | 0.015 | 0.150 | 0.075 | 0.075 |
| 13 | 450 | D | 0.015 | 0.150 | 0.075 | 0.075 |
| 14 | 423 | D | 0.015 | 0.150 | 0.060 | 0.090 |
| 15 | 423 | D | 0.01627 | 0.1627 | 0.0325 | 0.1175 |

| | | | Yield %* | | |
|---|---|---|---|---|---|
| Example | Temp. °C | Catalyst | Pyridine | 2-Picoline | 3-&4-Picoline |

TABLE I-continued

| | | | | | |
|---|---|---|---|---|---|
| 1 | 425 | A | 8.5 | 11.9 | 9.7 |
| 2 | 425 | A | 5.0 | 12.6 | 10.2 |
| 3 | 425 | A | 7.0 | 17.7 | 16.3 |
| 4 | 425 | B | 10.6 | 17.4 | 14.4 |
| 5 | 425 | B | 12.9 | 15.1 | 12.7 |
| 6 | 425 | B | 11.7 | 15.1 | 12.5 |
| 7 | 425 | B | 8.0 | 21.9 | 19.2 |
| 8 | 425 | B | 12.4 | 15.4 | 14.0 |
| 9 | 425 | C | 15.6 | 4.8 | 4.3 |
| 10 | 425 | C | 13.6 | 14.95 | 13.6 |
| 11 | 388 | D | 12.0 | 12.1 | 11.4 |
| 12 | 420 | D | 7.8 | 15.3 | 22 |
| 13 | 450 | D | 3.1 | 12.7 | 19.35 |
| 14 | 423 | D | 9.6 | 12.3 | 14.65 |
| 15 | 423 | D | 13.1 | 3.28 | 3.83 |

*Yield: Calculated as mole % carbon efficiencies, i.e., the yield expresses the percentage of the total Carlson in the feed material which ends up in each product, assuming that the other products had not been produced. Based on a stoichiometry of either 1 mole of pyridine or 1 mole of picoline being produced from 3 moles of acetaldehyde, then the maximum theoretical yield (i.e., carbon efficiency) to pyridine is 5/6 or 83.3%. The corresponding maximum for each picoline is 100%.
**AcH — acetaldehyde
'STP — standard temperature and pressure

EXAMPLES 16–18

In Examples 16–18 in Table II, below, further illustrating embodiment I, pure oxygen is used instead of air. The same reactor as in Table I, above, was used but the procedure was varied as follows: A liquid mixture of acetaldehyde and water was vaporized at a known rate and pure oxygen was mixed with the hot vapors just prior to entry into the reactor. The heated ammonia entered the bottom of the reactor via the second inlet port and mixed with the oxygen, steam and acetaldehyde vapors before passing over the catalyst. The flows of AcH, $H_2O$ and $NH_3$ were maintained constant and the oxygen flow was varied. The process was allowed to run continuously and an aliquot sample was removed for analysis at each different oxygen level.

TABLE II

| | | | Gaseous Flow Rates (STP) Mole/Hr/40 cc Catalyst | | | |
|---|---|---|---|---|---|---|
| Example | Temp. °C | Catalyst | AcH | $H_2O$ | $NH_3$ | $O_2$ |
| 16 | 400 | E | .05194 | 0.5194 | .2597 | .0463 |
| | | | .05194 | 0.5194 | .2597 | .060 |
| | | | .05194 | 0.5194 | .2597 | .070 |
| 17 | 400 | F | .05194 | .5194 | .2597 | .00535 |
| | | | .05194 | .5194 | .2597 | .0134 |
| | | | .05194 | .5194 | .2597 | .0268 |
| | | | .05194 | .5194 | .2597 | .0402 |
| | | | .05194 | .5194 | .2597 | .0535 |
| | | | .05194 | .5194 | .2597 | .067 |
| 18 | 400 | E | .05194 | .5194 | .2597 | .0402 |
| | | | .05194 | .5194 | .2597 | .0535 |
| | | | .05194 | .5194 | .2597 | .067 |
| | | | .05194 | .5194 | .2597 | .0803 |
| | | | .05194 | .5194 | .2597 | .1071 |

TABLE II-continued

| Example | °C | Catalyst | Pyridine | 2-Picoline | 4-Picoline |
|---|---|---|---|---|---|
| 16 | 400 | E | 26.3 | 6.5 | 5.85 |
| | | | 28.96 | 2.48 | 3.9 |
| | | | 24.58 | 1.15 | 1.7 |
| 17 | 400 | F | 0.7 | 33.65 | 28.25 |
| | | | 7.82 | 21.98 | 20.94 |
| | | | 18.36 | 11.67 | 12.31 |
| | | | 23.3 | 6.66 | 7.85 |
| | | | 23.7 | 3.67 | 5.25 |
| | | | 17.92 | 1.58 | 1.62 |
| 18 | 400 | E | 5.05 | 17.45 | 20.83 |
| | | | 10.81 | 12.38 | 13.43 |
| | | | 17.82 | 7.87 | 10.0 |
| | | | 21.38 | 5.18 | 6.90 |
| | | | 28.22 | 2.78 | 2.73 |

*Yield: Calculated as mole % carbon efficiencies, i.e., the yield expresses the percentage of the total Carlson in the feed material which ends up in each product, assuming that the other products had not been produced. Based on a stoichiometry of either 1 mole of pyridine or 1 mole of picoline being produced from 3 moles of acetaldehyde, then the maximum theoretical yield (i.e., carbon efficiency) to pyridine is 5/6 or 83.3%. The corresponding maximum for each picoline is 100%.

EXAMPLES 19–36

These examples illustrate embodiment II. A liquid feed mixture containing acetaldehyde, methanol and water is vaporized and passed at a controlled flow rate over a condensation catalyst maintained at an elevated temperature. The reactor described for Examples 1–15, above, was used, only prior to contacting the heated catalyst, the vaporized feed mixture is further mixed with a hot gaseous stream of ammonia and air. Reaction products are condensed in an ice-water cooled flask and analyzed by conventional techniques. Reaction conditions are given in the following Table III.

TABLE III

| | | Gaseous Flow Rates (STP) Mole/Hr/15 cc Catalyst | | | | |
|---|---|---|---|---|---|---|
| Example | Temp. °C | AcH | $H_2O$ | MeOH | $NH_3$ | Air |
| 19 | 423 | .01527 | .1374 | .01527 | .0775 | .0775 |
| 20 | 423 | .01527 | .1374 | .01527 | .0775 | .0775 |
| 21 | 423 | .01527 | .07634 | .07634 | .07634 | .07634 |
| 22 | 423 | .01527 | .07634 | .07634 | .07634 | .07634 |
| 23 | 390 | .01527 | .07634 | .07634 | .04581 | .1069 |
| 24 | 378 | .01386 | .1237 | .01386 | .0693 | .0693 |
| 25 | 400 | .01386 | .1237 | .01386 | .04158 | .09702 |
| 26 | 378 | .01386 | .1237 | .01386 | .04158 | .09702 |
| 27 | 350 | .01386 | .1237 | .01386 | .04158 | .09702 |
| 28 | 350 | .01386 | .1237 | .01386 | .04158 | .09702 |
| 29 | 350 | .01386 | .1237 | .01386 | .04158 | .09702 |
| 30 | 350 | .01414 | .0707 | .0707 | .0424 | .0989 |
| 31 | 378 | .01414 | .0707 | .0707 | .0424 | .0989 |

TABLE III-continued

| | | | | | | |
|---|---|---|---|---|---|---|
| 32 | 350 | .01637 | 0.00 | .1512 | .0796 | .0477 |
| 33 | 378 | .01687 | 0.00 | .1558 | .0796 | .0477 |
| 34 | 378 | .01687 | .1518 | .01566 | .05145 | .1200 |
| 35 | 378 | .01386 | .1237 | .01386 | .0693 | .0693 |
| 36 | 378 | .01386 | .1237 | .01386 | .0693 | .0693 |

| | | 100 × Moles Product Produced in 3.0 Hrs. | | | % Unreacted Methanol | Yield %* | | |
|---|---|---|---|---|---|---|---|---|
| Ex. | Cat. | Pyrid. | 2-Picol. | 3-&4-Picol. | Recovered | Pyrid. | 2-Picol. | 3-&4-Picol. |
| 19 | G | .4728 | .1127 | .122 | not measured | 17.2 | 4.92 | 5.33 |
| 20 | H | .6973 | .0667 | .1304 | '' | 25.37 | 2.90 | 5.7 |
| 21 | H | .8216 | .0184 | .345 | '' | 12.8 | 0.34 | 6.45 |
| 22 | J | .8354 | .029 | .224 | '' | 13.0 | 0.54 | 4.2 |
| 23 | J | 1.04 | trace | .256 | '' | 16.2 | trace | 4.8 |
| 24 | D | .5612 | .1622 | .1251 | 13.9 | 23.6 | 8.18 | 6.31 |
| 25 | D | .5321 | .0156 | .0621 | 5.6 | 21.74 | .77 | 3.04 |
| 26 | D | .6118 | .0768 | .0657 | 12.6 | 25.68 | 3.87 | 3.31 |
| 27 | D | .4884 | .080 | .0435 | 40.35 | 22.7 | 4.45 | 2.42 |
| 28 | J | .4354 | .1463 | .0450 | 38 | 20.0 | 8.07 | 2.48 |
| 29 | K | .3927 | .1436 | .0553 | 44.9 | 18.5 | 8.12 | 3.13 |
| 30 | K | .603 | .177 | .114 | 61.8 | 18.2 | 6.43 | 4.12 |
| 31 | K | .732 | .129 | .132 | 36.8 | 16.7 | 3.5 | 3.62 |
| 32 | K | .3688[a] | .1686[a] | .096[a] | 49.5 | 9.63 | 5.28 | 3.0 |
| 33 | K | .583[b] | .100[b] | .1184[b] | 17.7 | 7.88 | 1.63 | 1.92 |
| 34 | L | .434 | .0292 | .0362 | 15.4 | 18.48 | 1.49 | 1.85 |
| 35 | L | .418 | .1695 | .1327 | 12.26 | 17.47 | 8.5 | 6.65 |
| 36 | M | .4745 | .129 | .0866 | 24.3 | 20.7 | 6.76 | 4.53 |

*Yield: The % yields for Examples 19 to 23, inclusive, are calculated as % carbon efficiencies as defined for Tables I and II, above, based on the total number of carbon atoms contained in the acetaldehyde and methanol actually fed to the reactor. For examples 24 to 36, inclusive, the yields are calculated on the total amount of acetaldehyde fed to the reactor together with only that amount of methanol which was actually consumed. Based on a stoichiometry of 2 moles of acetaldehyde reacting with 1 mole each of methanol and ammonia, the theoretical yield (carbon efficiency) of pyridine is 100%.
[a] 100 × moles product produced in 2.0 hours
[b] 100 × moles product produced in 2.5 hours

EXAMPLES 37–40

These examples were carried out essentially as in Examples 16–18, above, except that the feed contained methanol as well as acetaldehyde and water and the remaining reaction conditions are as given in Table IV, below:

TABLE IV

| | | Gaseous Flow Rates (STP) Mole/Hr/40 cc Catalyst | | | | | | 100 × moles product produced in 1.0 hour | | | % unreacted methanol recovered | *Yield % | | |
|---|---|---|---|---|---|---|---|---|---|---|---|---|---|---|
| Expt. No. | Temp. °C. | AcH | H₂O | MeOH | NH₃ | O₂ | Catalyst | Pyrid. | 2-Picol. | 3-+4-Picol. | | Pyrid. | 2-Picol. | 3-+4-Picol. |
| 37 | 400 | .0482 | .482 | .0241 | 0.24 | .0268 | F | .4088 | .2301 | .222 | 13.5 | 23.2 | 15.7 | 15.2 |
| | | | | | | .0536 | | .4945 | .0665 | .0991 | 9.61 | 27.9 | 4.5 | 6.71 |
| 38 | 400 | .04812 | .4812 | .024 | .2406 | .0133 | F | 0.304 | 0.321 | 0.30 | | 13.17 | 16.72 | 15.2 |
| | | | | | | .0268 | | 0.336 | .260 | 0.28 | | 14.62 | 13.87 | 14.0 |
| | | | | | | .0401 | | 0.616 | 0.101 | 0.143 | | 26.9 | 5.3 | 7.52 |
| 39 | 400 | .045 | .45 | .09 | .24 | .0134 | E | 0.198 | 0.103 | 0.135 | 48.5 | 10.62 | 6.62 | 8.71 |
| | | | | | | .0268 | | 0.3616 | 0.143 | 0.204 | 41.6 | 12.4 | 5.9 | 8.38 |
| | | | | | | .0402 | | 0.5616 | 0.1179 | 0.2105 | 46.2 | 19.8 | 4.98 | 8.90 |
| | | | | | | 0.5356 | | 0.7816 | 0.0726 | 0.198 | 44.2 | 27.2 | 3.03 | 8.27 |
| | | | | | | .067 | | 0.884 | 0.0547 | 0.238 | 38.9 | 29.8 | 2.21 | 9.64 |
| | | | | | | .0803 | | 0.694 | 0.0449 | 0.142 | 36.6 | 23.1 | 1.8 | 5.68 |
| 40 | 400 | .0508 | .4812 | .0221 | .240 | .0402 | EE | 0.294 | 0.1795 | 0.1255 | 48.9 | 13.02 | 9.53 | 6.67 |
| | | | | | | .0535 | | 0.614 | 0.0992 | 0.147 | 36.3 | 26.55 | 5.15 | 7.63 |
| | | | | | | .067 | | 0.689 | 0.0439 | 0.100 | 36.7 | 29.8 | 2.27 | 5.2 |
| | | | | | | .0803 | | 0.662 | 0.0297 | 0.0678 | 32.2 | 28.4 | 1.52 | 3.49 |

*Yield: Calculated as in the case of Examples 24 to 36 above. (cf. footnote following Table III.)

EXAMPLE 41

A mixture of a 1:1 molar ratio of isobutyraldehyde (i-BuH) and acetaldehyde (AcH) is passed at a known rate through a pre-heater, and the resulting hot aldehydes mixed with known amounts of steam, air and ammonia, such that the mole ratio NH₃/aldehyde is 5:1, the air:aldehyde mole ratio is 10:1 and the steam:aldehyde mole ratio is 10:1. The mixture then passes over a silica-alumina-zinc oxide-HF catalyst at 470°C, such that the residence time over the catalyst is on the order of 7–8 seconds. Products are collected at 0°C and analysed by gas chromatography. The results of the run are shown in Table V, below:

TABLE V

| | | Gaseous Flow Rate (STP) Moles/Hr/50 cc Catalyst | | | | | 100 × Moles Product Produced in 1.75 Hrs. | | |
|---|---|---|---|---|---|---|---|---|---|
| Ex. | Temp. °C | AcH | iBuH | H₂O | NH₃ | Air | Pyrid. | 2-Picol. | 3-&4-Picol. |
| 41 | 470 | .06275 | .06275 | .6275 | .6275 | .6275 | 0.310 | 0.280 | 0.81 |

TABLE V-continued

| Ex. | Temp. °C | Pyrid. | Yield %* 2-Picol. | 3-&4-Picol. |
|---|---|---|---|---|
| 41 | 470 | 2.35 | 2.55 | 7.37 |

*Yield is calculated as a % carbon efficiency based on the total amount of carbon (AcH + iBuH) fed to the reactor.

It can be seen from the above examples in Tables I – V, inclusive, that embodiments I, II and III of the present invention provide very effective ways of preparing pyridine in significant percentage yields without the necessity for using formaldehyde. When methanol is used (cf. embodiment II) the substantial recoveries of unreacted methanol for recycle add considerably to the economy and efficiency of the instant discovery when compared to the drawbacks encountered with formaldehyde as a reactant.

It will be obvious to those skilled in the art that changes and variations can be made in carrying out the present invention without departing from the spirit thereof and, of course, the scope thereof as defined in the appended claims.

What is claimed is:

1. A method of preparing pyridine which consists essentially of reacting acetaldehyde, ammonia and oxygen in the presence of an aldehyde-ammonia condensation catalyst said catalyst being selected from the group consisting of alumina, silica, silica-alumina and silica-alumina metal oxides said metal oxides being selected from the group consisting of $ZrO_2$, $MgO$, $TiO_2$, $ThO_2$, $CuO$, $ZnO$, and $PbO$ at a temperature of from about 300° to about 550°C, ammonia being present in an amount of from 0.2 to about 15.0 mols/mol of acetaldehyde, and oxygen being present in an amount of from 0.1 to about 5.0 mols/mol of acetaldehyde.

2. The process of claim 1 wherein an inert diluent is present in the reaction medium.

3. The process of claim 2 wherein the inert diluent is steam.

4. The process of claim 2 wherein the inert diluent is present in an amount of from 1.0 to about 25.0 mols/mol of acetaldehyde.

* * * * *